United States Patent
Huber et al.

(10) Patent No.: US 9,046,464 B2
(45) Date of Patent: Jun. 2, 2015

(54) DEVICE AND METHOD FOR DETECTING A SUBSTANCE USING A THIN FILM RESONATOR (FBAR) HAVING AN INSULATING LAYER

(75) Inventors: Thomas Huber, München (DE); Martin Nirschl, Traunstein (DE); Dana Pitzer, Unterschleissheim (DE); Matthias Schreiter, München (DE)

(73) Assignee: SIEMENS AKTIENGESELLSCHAFT, Munich (DE)

( * ) Notice: Subject to any disclaimer, the term of this patent is extended or adjusted under 35 U.S.C. 154(b) by 1077 days.

(21) Appl. No.: 13/124,913
(22) PCT Filed: Sep. 29, 2009
(86) PCT No.: PCT/EP2009/062623
§ 371 (c)(1),
(2), (4) Date: Jun. 27, 2011
(87) PCT Pub. No.: WO2010/046212
PCT Pub. Date: Apr. 29, 2010

(65) Prior Publication Data
US 2011/0248700 A1    Oct. 13, 2011

(30) Foreign Application Priority Data
Oct. 21, 2008 (DE) .......... 10 2008 052 437

(51) Int. Cl.
*G01R 29/22* (2006.01)
*G01N 29/036* (2006.01)
*G01N 29/02* (2006.01)

(52) U.S. Cl.
CPC ............ *G01N 29/036* (2013.01); *G01N 29/022* (2013.01); *G01N 2291/0255* (2013.01); *G01N 2291/0256* (2013.01); *G01N 2291/0426* (2013.01)

(58) Field of Classification Search
CPC .............. G01N 29/022; G01N 29/036; G01N 2291/0426; G01N 2291/0256; G01N 2291/0255

USPC .......................................................... 324/109
See application file for complete search history.

(56) References Cited

U.S. PATENT DOCUMENTS 5,575,316 A * 11/1996 Pollklas ........................ 141/198
5,936,150 A    8/1999 Kobrin et al. ................ 73/24.06
(Continued)

FOREIGN PATENT DOCUMENTS

CN    1894583 A    1/2007    ............. G01N 29/02
CN    101010582 A    8/2007    ............. G01N 29/02
(Continued)

OTHER PUBLICATIONS

Chinese Office Action, Application No. 200980142045, 10 pages, Apr. 19, 2013.
(Continued)

Primary Examiner — Thomas F Valone
(74) Attorney, Agent, or Firm — King & Spalding L.L.P.

(57) ABSTRACT

A device for detecting at least one substance of a fluid, has a piezoacoustic thin film resonator with a piezoelectric layer on which electrode layers are arranged, and an adsorption surface for adsorbing the fluid substance, wherein the piezoelectric and electrode layers and the adsorption surface are designed and arranged on each other such that by electrically activating the electrode layers, an excitation alternating field can be coupled into the piezoelectric layer. The thin film resonator can be excited to a resonance oscillation frequency $f_R$ which depends on an amount of the substance adsorbed on the adsorption surface because of an excitation alternating field coupled into the piezoelectric layer. An electrical insulating layer is arranged directly on a side of one of the electrode layers facing away from the piezoelectric layer. Particularly advantageous is the combination of an aluminum electrode layer and a silicon dioxide insulating layer.

20 Claims, 2 Drawing Sheets

(56) References Cited

U.S. PATENT DOCUMENTS

| | | | |
|---|---|---|---|
| 6,429,571 B2* | 8/2002 | Raffalt et al. | 310/316.01 |
| 6,997,052 B2* | 2/2006 | Woehrle | 73/290 V |
| 7,146,845 B2* | 12/2006 | Raffalt | 73/1.83 |
| 2004/0197806 A1 | 10/2004 | Yoshida et al. | 435/6.11 |
| 2005/0148065 A1 | 7/2005 | Zhang et al. | 435/287.2 |
| 2006/0125489 A1 | 6/2006 | Feucht et al. | 324/633 |
| 2007/0145862 A1 | 6/2007 | Kimura et al. | 310/340 |
| 2007/0210349 A1 | 9/2007 | Lu et al. | 257/252 |
| 2009/0272193 A1 | 11/2009 | Okaguchi et al. | 73/657 |

FOREIGN PATENT DOCUMENTS

| | | | |
|---|---|---|---|
| CN | 101034083 A | 9/2007 | G01N 29/028 |
| CN | 101217266 A | 7/2008 | H03H 3/02 |
| DE | 10308975 A1 | 2/2004 | G01N 29/02 |
| DE | 10308975 B4 | 3/2007 | G01N 29/02 |
| JP | 2002372487 A | 12/2002 | G01N 5/02 |
| JP | 2004264023 A | 9/2004 | G01N 33/53 |
| JP | 2005533265 A | 11/2005 | G01N 27/00 |
| JP | 2006234685 A | 9/2006 | C12M 1/00 |
| JP | 2006337332 A | 12/2006 | G01N 5/02 |
| WO | 2008/102577 A1 | 8/2008 | G01N 5/02 |
| WO | 2010/046212 A1 | 4/2010 | G01N 29/02 |

OTHER PUBLICATIONS

L. Tessier et al., "Significance of mass and viscous loads discrimination for an AT-quartz blood group immunosensor", Sensors and Actuators B, 18-19, 1994, pp. 698-703; Magazine. (6 pages), 1994.

Gabl R et al: "First results on label-free detection of DNA and protein molecules using a novel integrated sensor technology based on gravimetric detection principles" Biosensors and Bioelectronics, Elsevier, BV, NL, vol. 19, No. 6, Sep. 11, 2003 pp. 615-620, XP002320316, ISSN: 0956-5663, all document; Others, Nov. 7, 2002.

International Search Report and Written Opinion for Application No. PCT/EP2009/062623 (13 pages), Jan. 15, 2010.

* cited by examiner

DEVICE AND METHOD FOR DETECTING A SUBSTANCE USING A THIN FILM RESONATOR (FBAR) HAVING AN INSULATING LAYER

CROSS-REFERENCE TO RELATED APPLICATIONS

This application is a U.S. National Stage Application of International Application No. PCT/EP2009/062623 filed Sep. 29, 2009, which designates the United States of America, and claims priority to German Application No. 10 2008 052 437.9 filed Oct. 21, 2008. The contents of which are hereby incorporated by reference in their entirety.

TECHNICAL FIELD

The invention relates to a device for detecting at least one substance of a fluid, comprising a piezoelectric thin film resonator having at least one piezoelectric layer, an electrode layer arranged on the piezoelectric layer, at least one further electrode layer arranged on the piezoelectric layer and at least one adsorption surface for adsorbing the substance of the fluid, wherein the piezoelectric layer, the electrode layers and the adsorption surface are designed and arranged on one another in such a way that by electrically activating the electrode layers an excitation alternating field can be coupled into the piezoelectric layer, the thin film resonator can be excited to a resonance oscillation at a resonance frequency $f_R$ because of an excitation alternating field coupled into the piezoelectric layer, and the resonance frequency $f_R$ depends on an amount of the substance adsorbed on the adsorption surface. In addition to the device, a method for detecting a substance using the device is specified.

BACKGROUND

A device of the type mentioned in the introduction is disclosed, for example, by DE 103 08 975 B4. The known device has, for example, a thin film resonator in which the electrode layer, the piezoelectric layer and the further electrode layer are stacked one above the other in a stratified formation. The piezoelectric layer consists, for example, of zinc oxide. The upper electrode layer (top electrode) is made of gold and has the adsorption surface for adsorbing the substance of the fluid. The thin film resonator is applied to a silicon substrate via the lower electrode layer (bottom electrode). For acoustic decoupling of the silicon substrate and the thin film resonator from one another, an acoustic mirror made of λ/4-thick layers of different acoustic impedance, for example, is arranged between them.

SUMMARY

According to various embodiments, the known device for detecting a substance can be developed in such a manner that a mass sensitivity is increased.

According to an embodiment, a device for detecting at least one substance of a fluid, comprises a piezoacoustic thin film resonator comprising at least one piezoelectric layer, an electrode layer arranged on the piezoelectric layer, at least one further electrode layer arranged on the piezoelectric layer and at least one adsorption surface for adsorbing the substance of the fluid, wherein the piezoelectric layer, the electrode layers and the adsorption surface are designed and arranged on one another in such a way that an excitation alternating field can be coupled into the piezoelectric layer by electrically activating the electrode layers, the thin film resonator can be excited to a resonance oscillation at a resonance frequency $f_R$ because of an excitation alternating field coupled into the piezoelectric layer, and the resonance frequency $f_R$ depends on an amount of the substance adsorbed on the adsorption surface, wherein at least one electrical insulating layer for electrically insulating the electrode layer is arranged directly on a side of at least one of the electrode layers facing away from the piezoelectric layer.

According to a further embodiment, the insulating layer may includes inorganic insulating material. According to a further embodiment, the inorganic insulating material may include at least one chemical compound selected from the group metal nitride and metal oxide. According to a further embodiment, the metal oxide can be silicon dioxide. According to a further embodiment, the electrode layer on which the insulating layer is arranged may include aluminum. According to a further embodiment, the thin film resonator can be arranged on a semiconductor substrate. According to a further embodiment, the thin film resonator can be arranged above a read-out circuit integrated in the semiconductor substrate. According to a further embodiment, the adsorption surface can be formed by the insulating layer. According to a further embodiment, the adsorption surface can be formed by a chemically sensitive coating applied to the insulating layer. According to a further embodiment, the chemically sensitive coating may include gold. According to a further embodiment, the chemically sensitive coating may have a layer thickness in the range from 5 nm to 30 nm.

According to another embodiment, a method for detecting at least one substance of a fluid using a device as described above, may comprise the following process steps: (a) bringing together the adsorption surface and the fluid in such a way that the substance can be adsorbed on the adsorption surface and (b) determining the resonance frequency of the thin film resonator.

BRIEF DESCRIPTION OF THE DRAWINGS

The invention is described in more detail below with reference to a number of exemplary embodiments and to the associated figures. The figures are schematic and are not true-to-scale representations.

DETAILED DESCRIPTION

Figure 1:
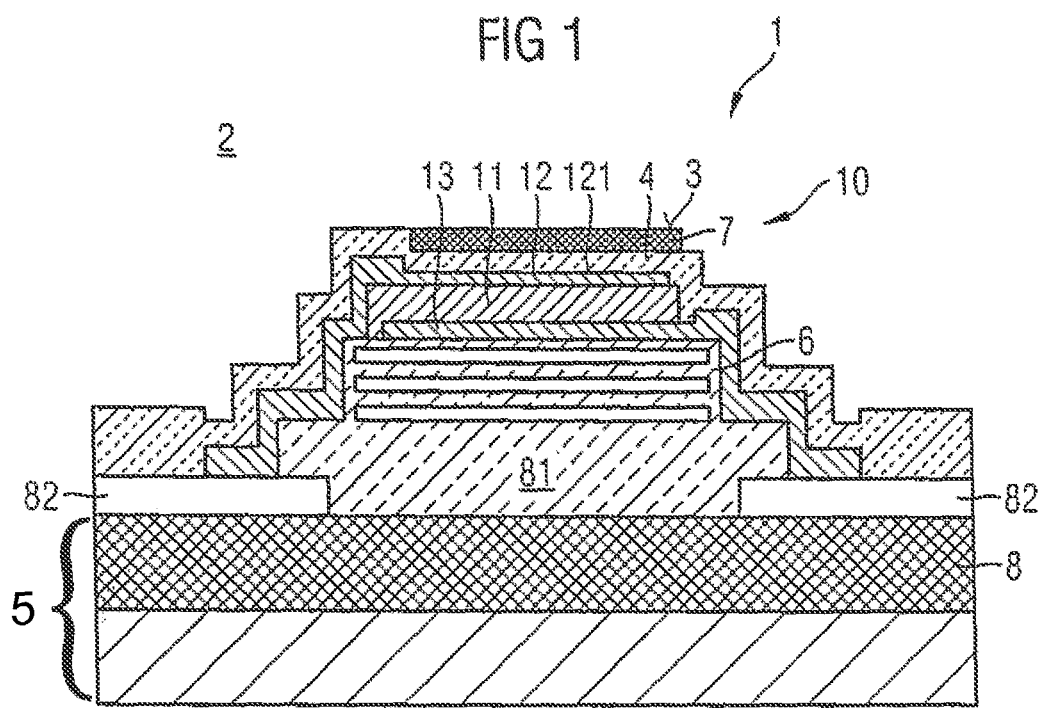
FIGS. 1 to 4 each show a respective embodiment of the device for detecting a substance of a fluid in a lateral cross-section.

According to various embodiments, a device for detecting at least one substance of a fluid is specified, comprising a piezoacoustic thin film resonator having at least one piezoelectric layer, an electrode layer arranged on the piezoelectric layer, at least one further electrode layer arranged on the piezoelectric layer and at least one adsorption surface for adsorbing the substance of the fluid, wherein the piezoelectric layer, the electrode layers and the adsorption surface are designed and arranged on one another in such a way that by electrically activating the electrode layers an excitation alternating field can be coupled into the piezoelectric layer, the thin film resonator can be excited to a resonance oscillation at a resonance frequency $f_R$ because of an excitation alternating field coupled into the piezoelectric layer and the resonance frequency $f_R$ depends on an amount of the substance adsorbed on the adsorption surface. The device is characterized in that at least one electrical insulating layer for electrically insulating the electrode layer is arranged directly on a side of at least one of the electrode layers facing away from the piezoelectric layer. In this case the insulating layer is preferably configured in such a manner that the fluid and the thin film resonator are separated completely from one another.

According to various embodiments, a method for detecting at least one substance of a fluid using the device and comprising the following process steps is also specified: a) bringing together the adsorption surface and the fluid in such a way that the substance can be adsorbed on the adsorption surface, and b) determining the resonance frequency of the thin film resonator.

The thin film resonator has, for example, a stratified structure comprising lower electrode layer, piezoelectric layer and upper electrode layer. The electrode layers are arranged on different sides of the piezoelectric layer. It is also possible that the electrode layers are arranged on one side of the piezoelectric layer.

The thin film resonator can be excited to thickness oscillations by electrically activating the electrode layers. With regard to a use for detecting a substance of a fluid, it is advantageous to design the piezoelectric layer in such a way that it can be excited to thickness shear oscillations as a result of the activation of the electrode layers. For a high mass sensitivity it is advantageous to select the resonance frequency $f_R$ from the range from 500 MHz to 10 GHz inclusive. For this purpose the layer thickness of the piezoelectric layer is selected from the range from 0.1 µm to 20 µm inclusive.

The piezoelectric layer is made, for example, of zinc oxide. Another suitable material is aluminum nitride, for example. The electrode layers preferably have layer thicknesses of less than 1 µm (e.g. 10 nm). Greater layer thicknesses of up to a few µm are also possible.

In a particular configuration, the insulating layer includes inorganic insulating material. In this case the insulating material may be of any desired kind. Preferably, however, the inorganic insulating material includes at least one chemical compound selected from the group metal nitride and metal oxide. For example, the insulating material is aluminum oxide ($Al_2O_3$) or silicon nitride ($Si_3N_4$). According to an embodiment, the metal oxide is silicon dioxide ($SiO_2$). Apart from a good electrical insulating capability, silicon dioxide is distinguished by low acoustic impedance and is therefore especially suitable for use with the thin film resonator.

The electrode layers are preferably made of aluminum. In a particular configuration, the electrode layer on which the insulating layer is arranged comprises aluminum. Aluminum is especially suitable as an electrode material for thin film resonators. Aluminum has low electrical resistance. Resistance noise is thereby minimized. Low acoustic impedance is also important. This leads to relatively high mass sensitivity, as does the low mass density of aluminum. In addition, aluminum is distinguished by high acoustic velocity. Phase components in the corresponding material are thereby kept small.

However, in addition to aluminum other materials and material combinations are also possible, as is a multilayer structure made of different materials.

The thin film resonator may be applied to any desired substrate (carrier). Preferably, the thin film resonator is arranged on a semiconductor substrate. A read-out circuit may be integrated in the semiconductor circuit. This is affected, for example, using CMOS (Complementary Metal Oxide Semiconductor) technology. With regard to a space-saving structure it is especially advantageous if the thin film resonator is arranged above a read-out circuit integrated in the semiconductor substrate. However, it is equally possible for the read-out circuit to be implemented via an SMD (Surface Mounted Device) component.

In a particular configuration the adsorption surface is formed by the insulating layer. This means that the insulating layer carries a biofunctionalization.

According to a particular configuration, however, the adsorption surface is formed by a chemically sensitive coating applied to the insulating layer. The chemically sensitive coating may be, for example, a plastics coating. In particular, the chemically sensitive coating includes gold. Preferably, the chemically sensitive coating is made of gold. A chemically sensitive coating made of gold is especially suited to biofunctionalization.

The chemically sensitive coating is applied to the insulating layer. The chemically sensitive coating therefore itself also contributes to the resonance frequency of the thin film resonator. Especially in the case of gold, a layer thickness as small as possible is advantageous with regard to a mass sensitivity as high as possible, because of the relatively high mass density. According to a particular device, the chemically sensitive coating has a layer thickness in the range from 5 nm to 30 nm. These layer thicknesses are entirely sufficient to achieve the necessary biofunctionalization. At the same time, because of the low mass of the chemically sensitive coating, a high mass sensitivity is achieved. The basis for this is a very high resonance frequency of the thin film resonator. With suitable materials and layer thicknesses, resonance frequencies in the range from 500 MHz to 10 GHz inclusive can be achieved.

The device may be used for analyzing gases or gas mixtures. Preferably, the device is used for detecting biomolecules in liquids.

To summarize, the following special advantages are obtained according to various embodiments:

- The device for detecting a substance of a fluid can be constructed very flexibly. Thus, the thin film resonator of the device is built up either on a wafer (for example of semiconductor material) or on CMOS read-out electronics, or on CMOS read-out electronics which are separated from the thin film resonator via an insulating layer (for example $SiO_2$).
- Especially with an above-mentioned electrode layer of aluminum, the following advantages are achieved: Resistance noise is minimized by the low electrical resistance. The low acoustic impedance of aluminum leads to increased mass sensitivity of the thin film resonator. The low mass density of aluminum has the same effect, resulting in very high mass sensitivity.

Aluminum is also distinguished by high CMOS compatibility. Integration in CMOS circuits is therefore simplified. For this purpose gold would be rather unsuitable, since it has low compatibility with CMOS circuits. In addition, it is distinguished by relatively high mass density. This leads to relatively low mass sensitivity.

- Because of the insulating layer, efficient electrical insulation of the thin film resonator and the fluid from one another is achieved.
- In the case of $SiO_2$ as the insulating material, the temperature coefficient of the resonance frequency is reduced; that is, the stability of the resonance frequency of the thin film resonator is increased with respect to temperature fluctuations.
- If a CVD process is used to apply the insulating layer, for example of $SiO_2$, the surface is smoothed. This causes a reduction of acoustic losses, especially in an application in water.
- The combination of electrode layer of aluminum and insulating layer of silicon dioxide is especially advantageous. The acoustic losses of aluminum and of silicon dioxide are less than those of gold, for example. This results in an approximately threefold increase in mass sensitivity. Because the materials aluminum and silicon dioxide contain fewer phase components than gold, for example, the piezoelectric layer can be made thicker for the same resonance frequency. As a result, higher phase proportions are present in the piezoelectric layer. This increases the effective piezoelectric coupling coefficient.

As a result of the greater thickness of the piezoelectric layer, the electrical capacitance of the thin film resonator is reduced, which is advantageous for many read-out circuits.

The device for detecting a substance of a fluid is a biosensor for detecting biomolecules. The biomolecules are parts of a DNA. Alternatively, biomolecules in the form of proteins are detected.

An essential component of the device 1 for detecting a substance of a fluid 2 is a piezoacoustic thin film resonator 10 with piezoelectric layer 11, electrode layer (top electrode) 12 and further electrode layer (bottom electrode) 13 stacked one above another. The piezoelectric layer is made of zinc oxide. A layer thickness of the zinc oxide layer is approximately 0.5 µm. The top electrode layer is made of aluminum and is approximately 100 nm thick. The bottom electrode layer is approximately 890 nm thick. A lateral extent of the thin film resonator is approximately 200 µm.

The thin film resonator is applied to an acoustic mirror 6 made of λ/4-thick layers having different acoustic impedance of a silicon substrate 5.

An electrical insulating layer 4 for electrically insulating the electrode layer 12 is arranged directly on a side 121 of the electrode layer 12 facing away from the piezoelectric layer. The insulating layer is approximately 100 nm thick and consists of silicon dioxide as the inorganic insulating material. In an alternative configuration the inorganic insulating material is silicon nitride. The insulating layer is applied using a CVD (Chemical Vapor Deposition) process.

Example 1

To form the adsorption surface 3 for adsorbing the substance of the fluid a chemically sensitive coating 7 of gold is applied to the insulating layer (FIG. 1). The coating has a functionalization for the biomolecules. The biomolecules can be adsorbed on the adsorption surface.

The thin film resonator is arranged above a read-out circuit 8 integrated in the substrate 5 using CMOS technology. For electrical insulation of the read-out circuit an insulating layer 81 is present between the acoustic mirror 5 and the read-out circuit 8. This insulating layer is made of silicon dioxide. For electrical activation the read-out circuit is connected to the electrode layers of the thin film resonator via the electrical contacts 82.

Example 2

Figure 2:
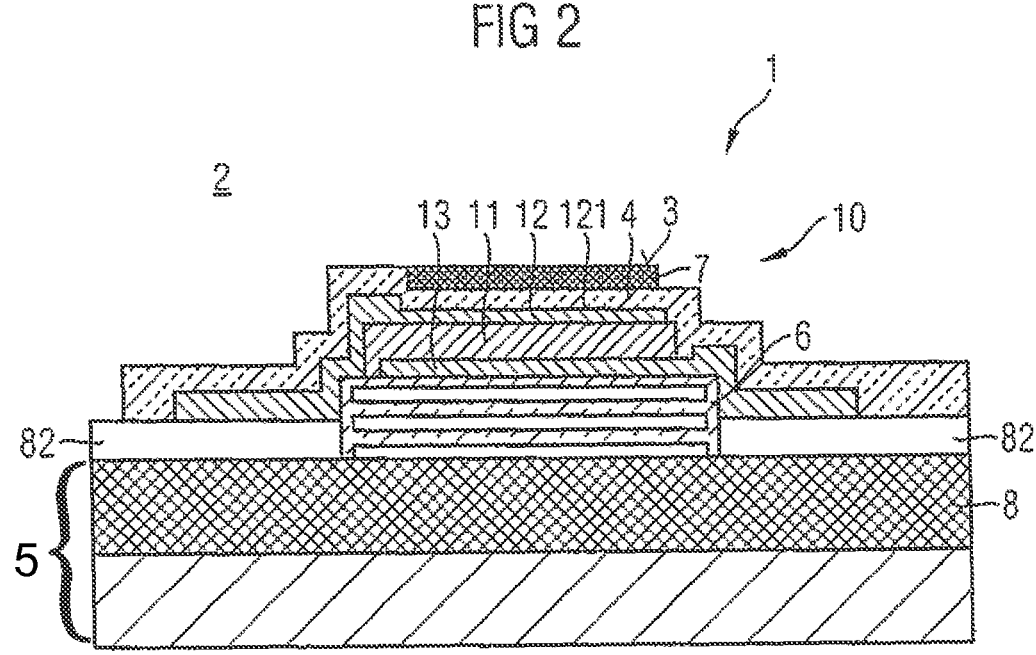

In contrast to the preceding example, no additional insulating layer is present between the acoustic mirror 6, on which the thin film resonator is arranged, and the read-out circuit 8 (FIG. 2).

Example 3

Figure 3:
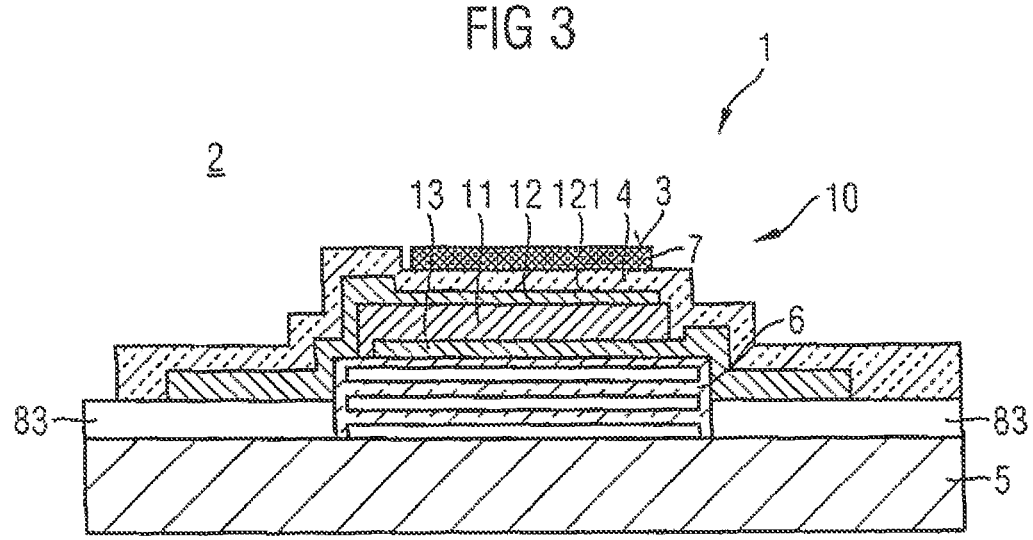
Figure 4:
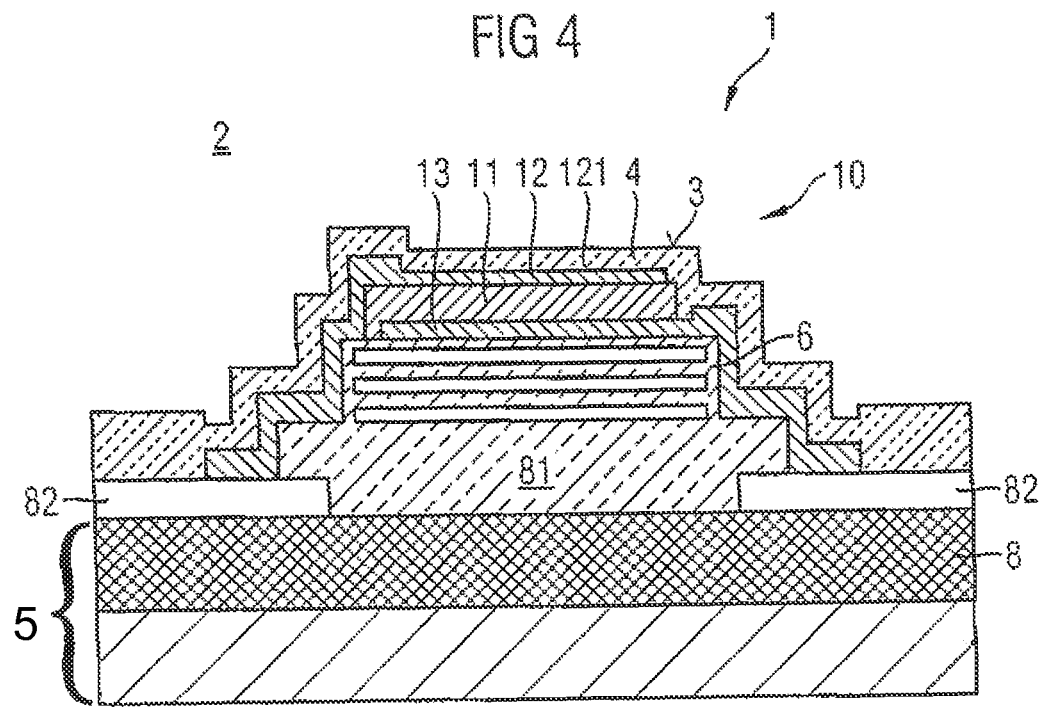

According to this example the thin film resonator is not arranged above a read-out circuit integrated in the silicon substrate (FIG. 3). An acoustic decoupling of the thin film resonator and the substrate is effected directly by means of the acoustic mirror. A read-out circuit (not shown) is either integrated at a different location of the semiconductor substrate or is implemented as an external component. This read-out circuit is electrically connected to the electrode layers of the thin film resonator via the contacts 83.

Example 4

This exemplary embodiment is derived from Example 1. In contrast to that embodiment, the insulating layer 4 forms the adsorption surface. The insulating layer has the biofunctionalization necessary for adsorption of the biomolecules.

Further exemplary embodiments are yielded by any desired combinations of the examples described.

What is claimed is:

1. A device for detecting at least one substance of a fluid, comprising a piezoacoustic thin film resonator comprising:
   at least one piezoelectric layer,
   a first electrode layer arranged on a first side of the piezoelectric layer, the first electrode layer having a side facing away from the piezoelectric layer,
   at least one second electrode layer arranged on a second side of the piezoelectric layer, and
   an electrical insulating layer arranged on the side of the first electrode layer facing away from the piezoelectric layer, the electrical insulating layer completely covering both the first and second electrode layers such that the fluid is completely prevented from contacting the first and second electrode layers,
   at least one adsorption surface for adsorbing the substance of the fluid, the at least one adsorption surface being physically separated from the first electrode layer by the electrical insulating layer,
   wherein the piezoelectric layer, the first and second electrode layers and the adsorption surface are designed and arranged relative to one another such that:
      an excitation alternating field is coupled into the piezoelectric layer by electrically activating the first and second electrode layers,
      the thin film resonator is excited to a resonance oscillation at a resonance frequency $f_R$ because of an excitation alternating field coupled into the piezoelectric layer, and
      the resonance frequency $f_R$ depends on an amount of the substance adsorbed on the adsorption surface.

2. The device according to claim 1, wherein the insulating layer includes inorganic insulating material.

3. The device according to claim 2, wherein the inorganic insulating material includes at least one chemical compound selected from the group metal nitride and metal oxide.

4. The device according to claim 3, wherein the metal oxide is silicon dioxide.

5. The device according to claim 1, wherein the first electrode layer on which the insulating layer is arranged includes aluminum.

6. The device according to claim 1, wherein the thin film resonator is arranged on a semiconductor substrate.

7. The device according to claim 6, wherein the thin film resonator is arranged above a readout circuit integrated in the semiconductor substrate.

8. The device according to claim 1, wherein the adsorption surface is formed by the insulating layer.

9. The device according to claim 1, wherein the adsorption surface is formed by a chemically sensitive coating applied to the insulating layer.

10. The device according to claim 9, wherein the chemically sensitive coating includes gold.

11. The device according to claim 9, wherein the chemically sensitive coating has a layer thickness in the range from 5 nm to 30 nm.

12. A method for detecting at least one substance of a fluid using a device comprising a piezoacoustic thin film resonator comprising at least one piezoelectric layer, a first electrode layer arranged on a first side of the piezoelectric layer and having a side facing away from the piezoelectric layer, at least one second electrode layer arranged on a second side of the piezoelectric layer, an electrical insulating layer arranged on the side of the first electrode layer facing away from the piezoelectric layer, the electrical insulating layer completely covering both the first and second electrode layers, and at least one adsorption surface for adsorbing the substance of the fluid, the at least one adsorption surface being physically separated from the first electrode layer by the electrical insulating layer, the method comprising the following steps:

bringing the fluid into contact with the adsorption surface such that the substance can be adsorbed on the at least one adsorption surface, completely preventing the fluid from contacting the first and second electrode layers by the electrical insulating layer, electrically activating the first and second electrode layers to couple an excitation alternating field into the piezoelectric layer, wherein the thin film resonator is excited to a resonance oscillation at a resonance frequency of the thin film resonator due to the excitation alternating field coupled into the piezoelectric layer, wherein the resonance frequency of the thin film resonator depends on an amount of the substance adsorbed on the adsorption surface, and determining the resonance frequency of the thin film resonator.

13. The method according to claim 12, wherein the insulating layer includes inorganic insulating material including at least one chemical compound selected from the group consisting of metal nitride and silicon dioxide.

14. The method according to claim 12, wherein the first electrode layer on which the insulating layer is arranged includes aluminum.

15. The method according to claim 12, wherein the thin film resonator is arranged on a semiconductor substrate.

16. The method according to claim 15, wherein the thin film resonator is arranged above a read-out circuit integrated in the semiconductor substrate.

17. The method according to claim 12, wherein the adsorption surface is formed by the insulating layer.

18. The method according to claim 12, wherein the adsorption surface is formed by a chemically sensitive coating applied to the insulating layer.

19. The method according to claim 18, wherein the chemically sensitive coating includes gold.

20. The device according to claim 18, wherein the chemically sensitive coating has a layer thickness in the range from 5 nm to 30 nm.

* * * * *